United States Patent [19]

Barberet et al.

[11] Patent Number: Plant 5,516

[45] Date of Patent: Jul. 16, 1985

[54] CARNATION NAMED LONDANELLE

[75] Inventors: Nicole Barberet; Yves Ducloux, both of Antibes, France

[73] Assignee: Laboratoire de Physiologie Vegetale de la Londe SCS, La Londe, France

[21] Appl. No.: 512,475

[22] Filed: Jul. 11, 1983

[51] Int. Cl.[3] ..... A01H 5/00

[52] U.S. Cl. ..... Plt./73

[58] Field of Search ..... Plt./73

*Primary Examiner*—Robert E. Bagwill

*Attorney, Agent, or Firm*—Chas. W. Rummler

[57] ABSTRACT

A new red carnation variety of the tall, many stemmed type, in which the blooms are borne singly on long, strong stems, the plant having a vigorous growth habit blooming recurrently in the midseason of Spring and Fall with a profuse production of flowers of medium size and a middle red coloration.

1 Drawing Figure

BACKGROUND OF THE NEW PLANT

This new carnation plant was developed by us during the course of breeding efforts carried on at La Londe, Les Maures, France, since 1977 with the object of producing a greenhouse carnation plant having good quality of flower, stem and growth habit and a resistance to the Fusarium Oxysporum disease. Our new plant originated as a seedling resulting from our crossing of selected varieties from breeding stock maintained by us at La Londe, France, and was discovered by us in 1977 as possessing characteristics of a plant having favorable marketing merit.

Because of the apparently favorable characteristics of this seedling we propagated it at La Londe, by means of cuttings, for testing purposes and such propagation was carried on under our direction through several successive generations. From this we found that the favorable characteristics of our new variety held true from generation to generation and appeared to be firmly fixed.

DESCRIPTION OF THE DRAWING

Our new variety of carnation is illustrated by the accompanying photographic drawing which shows, in full color, a typical arrangement of buds and flowers in various stages of opening, the colors depicted being as nearly true to those herein specified as it is reasonably possible to obtain by conventional professional photographic procedures.

DESCRIPTION OF THE NEW PLANT

The following is a detailed description of our new carnation variety based upon observations made early in 1983 of plants grown in greenhouse at La Londe, France, the color designations being according to The R.H.S. Colour Chart of The Royal Horticultural Society at London, England.

THE PLANT

Origin: Seedling.

Parentage:

*Seed parent.*—Stock Variety 73 R 24 (unpatented).

*Pollen parent.*—Stock Variety 73 R 19 (unpatented). These are unnamed varieties individually identified in our permanent records and maintained for breeding purposes.

Classification:

*Botanic.*—*Dianthus caryophyllus.*

*Commercial.*—Standard Carnation.

Form: Tall, leafy bush.

Height (at 8 months): About 113 cm.

Main stem length: Less than 15 cm. due to pinching.

Branching character: At least four stems emitted near the ground.

Growth: Vigorous, upright and very strong.

Foliage:

*Quantity.*—Medium.

*Number of leaves.*—More than 120.

Size of leaf.—At seventh node, about 11.5 cm. long and 1 cm. wide.

*Shape.*—Linear with upwardly curved margins.

*Texture.*—Leathery.

*Color.*—Upper side — 189A. Under side — 189A.

*Ribs, veins and rachis.*—Hardly noticeable.

THE BUD

Shape: Ovoid.

Size: Medium.

*Diameter.*—About 2.1 cm.

*Length.*—About 3.3 cm.

Rate of opening: Slow.

Color of petals:

*When sepals first divide.*—Same as full bloom.

*When petals begin to unfurl.*—Same as full bloom.

Sepals:

*Number.*—Five.

*Shape.*—Generally ovate but joined at the lower part and having an acuminate apex. The sepals are hooded over the bud and stand up when the flowers open.

*Color.*—Inside — Greenish White. Outside — 137C and 143C.

*Striae.*—Longitudinal

Calyx:

*Shape.*—Long bell-shaped.

*Size.*—Medium.

*Splitting.*—Calyx does not split.

*Aspect.*—Moderately glandular.

Flower stem:

*Length.*—About 69 cm.

*Character.*—Erect and rigid.

*Color.*—189B.

THE FLOWER

Blooming habit: Recurrent and profuse in midseason of Spring and Fall.

Size of bloom: Medium.

*Diameter.*—Average about 8 cm.

*Depth.*—Average about 6.6 cm.

Borne: Singly.

Shape:

*When bloom first opens.*—High centered.

*When bloom matures.*—Dome shaped.

Petalage:

*Number of petals.*—52 to 74, averaging about 60.

*Arrangement.*—Imbricated.

*Form.*—Fan shaped with flat margins and deeply serrated outer end.

*Texture.*—Soft.

*Appearance.*—Satiny.

*Color.*—Outer petal: Body — 45B and 45C at petal tips. Base — Greenish White. Reverse side — 45D and 47D. Inside petal: Body — 45B with 45C at petal tips. Base — Greenish White. Reverse side — 45D and 47D.

Petaloids: From 1 to 14 in number.

*Size.*—Smaller than petals.

*Color.*—The same as the petals. p0 Flower stem:

*Length.*—About 69 cm. (cut at tenth node).

*Character.*—Upright with very good strength.

*Color.*—189B.

Fragrance: Fragrance is present.

Persistence: Petals hang on and dry.

Lasting quality: At least ten days in vase keeping.

Disease resistance: This plant is resistant to *Fusarium oxysporum* as observed INRA, Antibes, Alpes-Maritimes, France.

REPRODUCTIVE ORGANS

Stamens:

*Number.*—6 to 14.

*Arrangement.*—Around the pistils.

*Anthers.*—Size: Less than 4 mm. Color: Whitish.

*Filaments.*—Color — Whitish.

Pistils:

*Number.*—3 to 5.

*Styles.*—Color — White.

*Stigmas.*—Color — Light Red.

Characteristic of ovaries: Ribbed ovary.

Although the range of red carnations comprises numerous varieties, the present discovery is distinguished, not only by the manner of its origin, but also by the characteristics of its flowers. When compared with "Scania" (unpatented) our present discovery has petals that are more serrated and the flower stems are straighter, the calyx never splits and the plant is tolerant to *Fusarium oxysporum.*

We claim:

1. The new and distinct variety of carnation plant, substantially as herein shown and described, characterized by its recurrent and profuse production of medium sized, bright red blossoms carried on strong, straight stems.

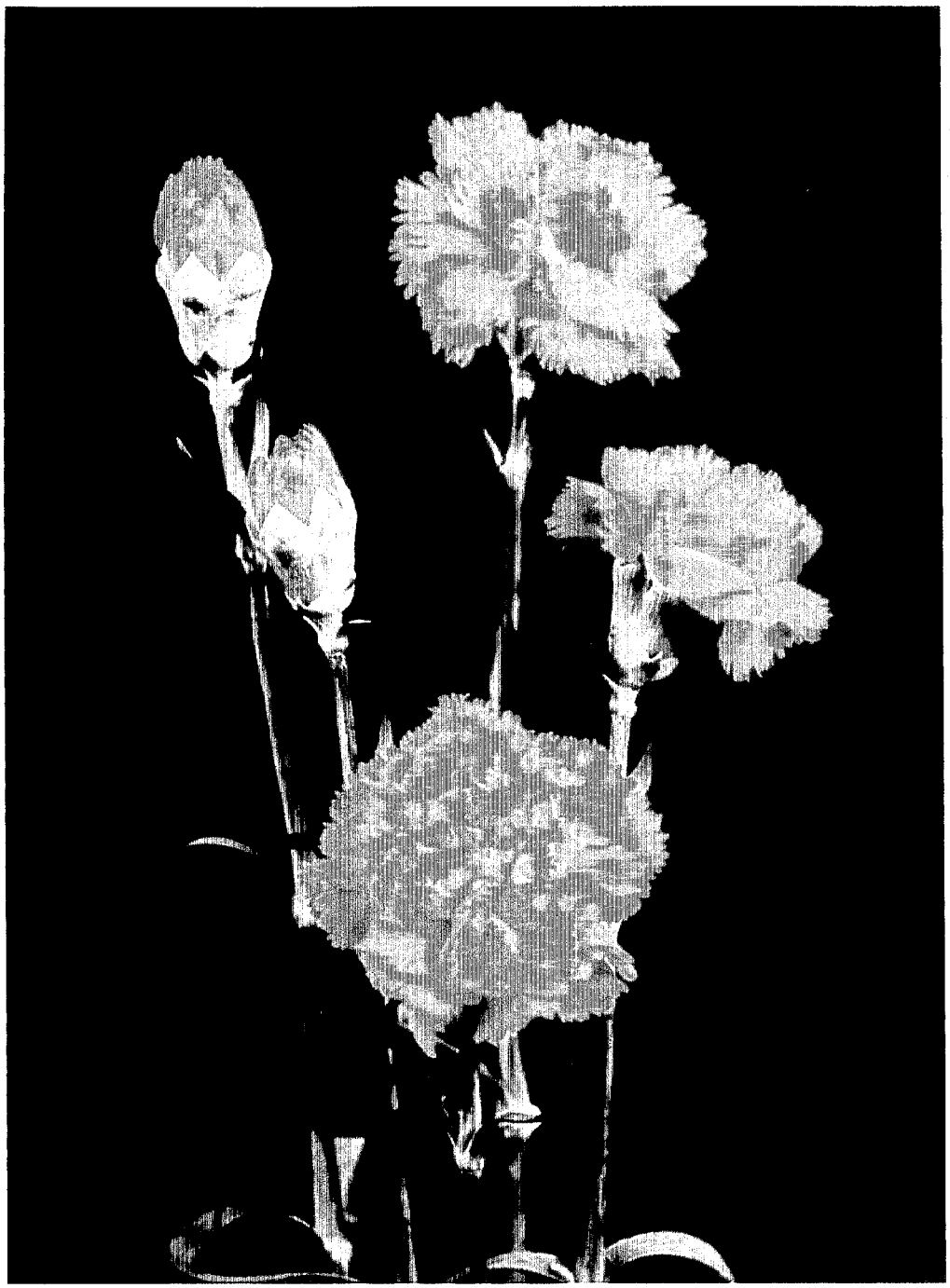

* * * * *